United States Patent [19]
Theriot

[11] Patent Number: 5,998,627
[45] Date of Patent: Dec. 7, 1999

[54] PREPARATION AND USES OF HYDROCARBYLNITRONES

[75] Inventor: Kevin J. Theriot, Baton Rouge, La.

[73] Assignee: Albemarle Corporation, Richmond, Va.

[21] Appl. No.: 08/905,525

[22] Filed: Aug. 4, 1997

[51] Int. Cl.[6] .................. C07D 263/04; C07C 249/02; C07C 249/00
[52] U.S. Cl. ............ 548/240; 564/248; 564/271; 564/272; 564/275; 564/278
[58] Field of Search .............. 548/240; 564/248, 564/271, 272, 275, 278

[56] References Cited

PUBLICATIONS

Mitsui, et al., "Tungstate Catalysed Oxidation of Secondary Amines with Hydrogen Peroxide. A Novel Transformation of Secondary Amines into Nitrones", J. Chem. Soc., Chem. Commun., 1984, pp. 874–875.

Murahashi, et al., "Tungstate–Catalyzed Oxidation of Secondary Amines to Nitrones. α–Substitution of Secondary Amines via Nitrones", J. Org. Chem., 1990, vol. 55, pp. 1736–1744.

Katritzky, et al., "The conversion of primary amines into nitrones: an extension of the Kröhnke reaction", Journal of the Royal Netherlands Chem. Soc., vol. 102/1, 1983, pp. 51–54.

S. Wawzonek et al., "Intermediates in the reaction of Grignard reagents with nitromethane", Journal of Organic Chemistry, vol. 38, No. 16, 1973 pp. 2763–2766.

S. Sakaue et al., "Oxidation of aliphatic and aromatic amines with hydrogen peroxide catalyzed by peroxoheteropoly oxometalates", Chemistry Letters, 1992 pp. 289–292.

*Primary Examiner*—Peter O'Sullivan
*Attorney, Agent, or Firm*—Philip M. Pippenger

[57] ABSTRACT

Nitrones are produced by reaction of primary amine with aldehyde or ketone, in the presence of a transition metal-containing oxidation catalyst, and a peroxidic compound. The nitrone can then be reacted with a vinylaromatic compound to produce a 2-hydrocarbyl-5-arylisoxazolidine. Both such reactions can be conducted concurrently by including the vinylaromatic compound in the initial reaction mixture. Hydrogenation of the 2-hydrocarbyl-5-arylisoxazolidine, e.g., using hydrogen and a palladium-carbon catalyst, forms an N-hydrocarbyl-3-aryl-3-hydroxypropylamine. Such reactions enable, inter alia, synthesis of the racemic hydrochloride salt of N-methyl-3-phenyl-3-[4-trifluoromethyl)phenoxy]-propylamine, known generically as fluoxetine hydrochloride, a widely used antidepressant.

55 Claims, No Drawings

PREPARATION AND USES OF HYDROCARBYLNITRONES

TECHNICAL FIELD

This invention relates to a process for the preparation of hydrocarbylnitrones and the use thereof in the synthesis of substituted amines, such as N-hydrocarbyl-3-phenyl-3-[4-trifluoromethyl)phenoxy]propylamine and acid addition salts thereof. The racemic hydrochloride salt of N-methyl-3-phenyl-3-[4-trifluoromethyl)phenoxy]propylamine, known generically as fluoxetine hydrochloride, is a widely used antidepressant.

BACKGROUND

It is indicated in the literature (U.S. Pat. No. 4,596,874; *J. Chem. Soc., Chem. Commun.*, 1984, 874; and *J. Org. Chem.*, 1990, 55, 1736) that oxidation of secondary amines with hydrogen peroxide and sodium tungstate gives good yields of nitrones. However, when using dimethylamine in this manner, a considerable amount of N,N-dimethylformamide was produced as a co-product.

THE INVENTION

In accordance with one aspect of this invention there is provided a novel process for producing hydrocarbylnitrones of the formula:

(I)

where R is a hydrocarbyl group, such as alkyl, alkenyl, cycloalkyl, cycloalkenyl, aryl, aralkyl, or the like, which will typically contain, independently, up to about 18 carbon atoms, and each R' is, independently, a hydrogen atom or a hydrocarbyl group, such as alkyl, alkenyl, cycloalkyl, cycloalkenyl, aryl, aralkyl, or the like, each of which will typically contain, independently, up to about 18 carbon atoms. The process comprises mixing together (i) one or more primary amines, (ii) one or more aldehydes or ketones, (iii) a transition metal-containing oxidation catalyst, and (iv) a peroxidic compound; and concurrently or subsequently, subjecting the resultant mixture to reaction conditions effective to form a reaction mixture in which a hydrocarbylnitrone has been formed. When ingredient (ii) is formaldehyde or a formaldehyde precursor such as formalin, paraformaldehyde, etc., the product of the reaction is an N-hydrocarbylnitrone (R is a hydrocarbyl group and each R' group is a hydrogen atom). When ingredient (ii) is an aldehyde other than formaldehyde (i.e., an aldehyde of the formula R"CHO where R" is hydrocarbyl having 1 or more carbon atoms), the product of the reaction is an N,α-dihydrocarbylnitrone (R and one R' group are, independently, hydrocarbyl groups and the other R' group is a hydrogen atom). And when ingredient (ii) is a ketone, the product of the reaction is an N,α,α-trihydrocarbylnitrone (R and the two R' groups are, independently, hydrocarbyl groups). It will be appreciated that in some instances where proton transfer can occur leading to a more stable product, the foregoing initial product of the reaction may undergo such transformation. To illustrate, it is not inconceivable that N-benzylnitrone (formed by reaction of benzyl amine with formaldehyde) may under appropriate reaction conditions undergo an internal rearrangement to form N-methyl-α-phenylnitrone.

It will thus be seen that the number of hydrocarbyl substituents in the nitrone being formed is dependent upon whether (A) formaldehyde (or precursor thereof), or (B) an aldehyde having a hydrocarbyl group, or (C) a ketone is used as the reactant in the process. Therefore, unless the context indicates otherwise, the term "hydrocarbylnitrone" is used in this specification and in the appended claims to refer collectively to the nitrones formed when using any one, or any two, or all three of (A), (B), and (C) of this paragraph.

Another aspect of this invention is a process of synthesizing 2-hydrocarbyl-5-arylisoxazolidines which comprises (a) forming a hydrocarbylnitrone of Formula (I) above from a primary amine and an aldehyde or ketone in the manner described above, and (b) either concurrently or subsequently causing the hydrocarbylnitrone to react with one or more vinylaromatic compounds under reaction conditions effective to form a reaction mixture in which a 2-hydrocarbyl-5-arylisoxazolidine has been formed. It will be seen, therefore, that this invention provides both a one-step process and a two-step process for preparing 2-hydrocarbyl-5-arylisoxazolidines.

All available chemical evidence indicates that whether the process is conducted in one step or as a two-step operation, the 2-hydrocarbyl-5-arylisoxazolidine is formed by a cycloaddition reaction between the vinylaromatic compound and the hydrocarbylnitrone. The number and position(s) of hydrocarbyl groups in the 2-hydrocarbyl-5-arylisoxazolidine formed in this reaction depends upon the identities of the two R' groups in the initial hydrocarbylnitrone (which in turn depend upon the aldehyde or ketone used in the reaction with the primary amine). If both R' groups of the hydrocarbyl nitrone are hydrogen atoms, then the product of the reaction from (b) will be a 2-hydrocarbyl-5-arylisoxazolidine. If one such R' is hydrocarbyl and the other R' is a hydrogen atom, the product of the reaction from (b) will be a 2,3-dihydrocarbyl-5-arylisoxazolidine. And if both such R' groups are hydrocarbyl groups, the product of the reaction from (b) will be a 2,3,3-trihydrocarbyl-5-arylisoxazolidine. The hydrocarbyl group in the 2-position is derived from the primary amine, and the hydrocarbyl group or groups in the 3-position are derived, respectively, from the aldehyde or ketone used. Reactions in which both R' groups are hydrogen atoms are preferred, and thus the reaction in (a) preferably involves formaldehyde or a formaldehyde precursor such as formalin, paraformaldehyde, or the like, with the primary amine.

Because the number and position(s) of the hydrocarbyl substitution on the 5-arylisoxazolidine compound being formed is dependent upon the structure of the hydrocarbylnitrone (which as noted above depends on whether (A) formaldehyde (or precursor thereof), or (B) an aldehyde having a hydrocarbyl group, or (C) a ketone was used as the reactant in forming the hydrocarbylnitrone), and unless the context indicates otherwise, the term "2-hydrocarbyl-5-arylisoxazolidine" is used in this specification and in the appended claims to refer collectively to the products of the one-step and two-step reactions between the hydrocarbylnitrone and the vinylaromatic compound.

As noted above, the available chemical evidence indicates that the 2-hydrocarbyl-5-arylisoxazolidine is formed by a cycloaddition reaction between the vinylaromatic compound and the hydrocarbylnitrone. However, since one cannot actually see the molecules as they are reacting, one necessarily has to rely upon chemical theory and whatever evidence can be adduced in the laboratory. Therefore it is deemed prudent in view of the vicissitudes of jurisprudence to also describe this aspect of the invention in another way, namely, as a process which comprises mixing together as ingredients (i) one or more primary amines, (ii) one or more aldehydes and/or ketones (preferably formaldehyde or a formaldehyde precursor such as formalin, paraformaldehyde, or the like), (iii) a transition metal-containing oxidation catalyst, (iv) a peroxidic compound, and optionally, but preferably, (v) a vinylaromatic compound; and concurrently or subsequently, subjecting the mixture to reaction conditions effective to form a reaction mixture in which:

A) if a vinylaromatic compound was included as an ingredient used in forming the mixture, a 2-hydrocarbyl-5-arylisoxazolidine has been formed, or B) if a vinylaromatic compound was not included as an ingredient used in forming the mixture, a hydrocarbylnitrone has been formed, and in which case the process further comprises mixing together as ingredients (i) at least a portion of said reaction mixture, and (ii) a vinylaromatic compound; and concurrently or subsequently, subjecting the mixture to reaction conditions effective to form a reaction mixture in which a 2-hydrocarbyl-5-arylisoxazolidine has been formed.

By conduct of the process of this invention in a preferred manner, yields of 2-hydrocarbyl-5-arylisoxazolidine as high as 46%, based on methylamine, have been achieved.

Other embodiments of this invention will become still further apparent from the ensuing description and appended claims.

Nitrone Synthesis

The process for producing hydrocarbylnitrone involves reaction in a mixture formed from primary amine, aldehyde or ketone, a transition metal-containing oxidation catalyst, and a peroxidic compound.

Primary amines used in the process typically contain in the range of 1 to about 18 carbon atoms in the molecule. The hydrocarbyl group can have any suitable structure such as alkyl, alkenyl, alkynyl, cycloalkyl, cycloalkenyl, aryl, aralkyl, etc., and the ring(s) of cyclic groups can be substituted by one or more aliphatic, cycloaliphatic or aromatic hydrocarbyl groups and/or may be fused with another ring which itself may be substituted in this manner. Preferred are monoalkylamines in which the alkyl group has in the range of 1 to about 18 carbon atoms and more preferably in the range of 1 to about 8 carbon atoms, and in either case the alkyl group can be a primary, secondary or tertiary alkyl group, with primary alkyl groups being most preferred. Especially preferred is methylamine.

Generally speaking, aldehydes (R"CHO where R" is a hydrogen atom or a hydrocarbyl group of the types described in the immediately preceding paragraph) and ketones (R"COR" where each R" is, independently, a hydrocarbyl group of the types described in the immediately preceding paragraph) are suitable for use in the process. Thus except for the case of formaldehyde where R" is a hydrogen atom, R" contains in the range of 1 to about 18 carbon atoms and more preferably in the range of 1 to about 8 carbon atoms. The more preferred aldehydes include formaldehyde, acetaldehyde, propionaldehyde and butryaldehyde, with formaldehyde and formaldehyde precursors being most preferred. Of the ketones, acetone, 2-butanone, 2-pentanone, 3-pentanone, 2-hexanone, 3-hexanone, 3-heptanone, 4-heptanone, 4-octanone, and 4-nonanone are preferred, with acetone and 2-butanone being the most preferred ketones.

Suitable reaction conditions typically include exposing the mixture to one or more temperatures in the range of about 0 to about 100° C. Proportions are typically chosen such that from about 1.0 to about 1.2 moles of peroxidic compound are fed to the reaction mixture per mole of primary amine being used. Catalytically effective amounts of the transition metal-containing catalyst typically fall in the range of about 0.1 to about 5.0 mol % based on moles of the primary amine. Suitable peroxidic compounds include hydrogen peroxide, alkyl hydroperoxides, aryl hydroperoxides, and the like. Aqueous hydrogen peroxide of at least 10% concentration is a preferred reagent for use in the process. Satisfactory yields of the nitrone are usually achieved within the range of about 0.25 to about 2.0 hours. The reaction is typically conducted in a suitable inert solvent such as water, methanol, ethanol, 2-propanol, or the like, including mixtures of such solvents.

Examples 1–5, wherein percentages are by weight unless otherwise specified, illustrate the practice and advantages of the nitrone synthesis of this invention, and are not to be construed as constituting limitations on the invention.

EXAMPLE 1

30% Hydrogen peroxide (1.1 g, 9.7 mmol) was added dropwise to 40% aqueous $Me_2NH$ (1.0 g, 8.9 mmol) in $H_2O$ (7.0 g) with moderate cooling. This mixture was then transferred to an addition funnel and 30% $H_2O_2$ (1.1 g, 9.7 mmol), saturated aqueous $Na_2CO_3$ (1.1 g), and $Na_2WO_4 \cdot 2H_2O$ (0.1 g, 1.5 mmol) were added to the flask. The solution in the addition funnel was then added dropwise to maintain the temperature at 40–50° C. After the addition, the reaction was allowed to cool to 20° C. and analyzed by $^1H$ NMR which showed N-methylnitrone as the major product (along with DMF and formaldoxime).

EXAMPLE 2

30% Hydrogen peroxide (17.0 g, 150 mmol) was added dropwise to 40% aqueous $Me_2NH$ (13.5 g, 120 mmol) in $H_2O$ (94.5 g) with moderate cooling. This mixture was then transferred to an addition funnel and 30% $H_2O_2$ (23.5 g, 209 mmol), saturated aqueous $NaHCO_3$ (40 g), and $Na_2WO_4 \cdot 2H_2O$ (1.3 g, 3.9 mmol) were added to the flask. The solution in the addition funnel was then added dropwise to maintain the temperature at 40–50° C. After the addition, the reaction was allowed to cool to 20° C. and analyzed by $^1H$ NMR which showed N-methylnitrone (30%) as the major product (along with DMF and formaldoxime).

EXAMPLE 3

40% Aqueous dimethylamine (10.0 g, 88.9 mmol) and saturated $NaHCO_3$ (80.0 g) were cooled to 5–10° C. 50% Hydrogen peroxide (6.0 g, 88 mmol) was added dropwise so as to maintain the temperature <10° C. $Na_2WO_4 \cdot 2H_2O$ (1.0 g, 3.0 mmol) in $H_2O$ (3.0 g) was added dropwise followed by a second addition of $H_2O_2$ (6.0 g, 88 mmol). The solution was then analyzed by $^1H$ NMR which showed N-methylnitrone as the major product (along with DMF and formaldoxime).

EXAMPLE 4

40% Aqueous $Me_2NH$ (40.0 g, 356 mmol) and saturated aqueous $NaHCO_3$ (160 g) were cooled to 5–10° C. 50% Hydrogen peroxide (24.0 g, 353 mmol) was added dropwise to maintain the temperature. A solution of 50% Hydrogen peroxide 24.0 g, 353 mmol) and $Na_2WO_4 \cdot 2H_2O$ (4.0 g, 12 mmol), and saturated aqueous NaHCO$_3$ (160 g) was added dropwise to maintain the temperature. The solution was stirred for several hours. $^1$H NMR analysis showed mainly nitrone formation along with DMF and formaldoxime.

EXAMPLE 5

A solution of 40% aqueous Me$_2$NH (40.0 g, 356 mmol) and NaHCO$_3$ (12.3 g, 146 mmol) in water (148 g) was cooled to 0° C. 50% Hydrogen peroxide (24.0 g, 353 mmol) was added dropwise to maintain the temperature. A solution of NaHCO$_3$ (12.3 g, 146 mmol) and Na$_2$WO$_4$.2H$_2$O (4.0 g, 12 mmol) in water (148 g) was added slowly. An additional amount of 50% H$_2$O$_2$ (32.0 g, 471 mmol) was slowly added. $^1$H NMR analysis showed mainly nitrone formation (38%) along with DMF and formaldoxime.

Arylisoxazolidine Synthesis

In a two step synthesis, the hydrocarbylnitrone formed in the first step (i.e., step (a), the nitrone synthesis described above) and vinylaromatic compound are caused to react to produce the 2-hydrocarbyl-5-arylisoxazolidine. If desired, the hydrocarbylnitrone formed in the first step can be isolated from the reaction mixture formed in the first step. Preferably, however, in conducting the second step (i.e., step (b) wherein the 2-hydrocarbyl-5-arylisoxazolidine is to be formed), a mixture is formed from (i) all or a portion of the reaction mixture from step (a), (ii) a peroxidic compound, and (iii) a transition metal-containing oxidation catalyst. At the same time this mixture of (i), (ii), and (iii) is being formed and/or subsequent to the formation of this mixture of (i), (ii), and (iii), this mixture is maintained at or subjected to appropriate reaction conditions such that 2-hydrocarbyl-5-arylisoxazolidine is produced in suitable yield. The transition metal-containing oxidation catalyst charged to the reaction mixture in step (a) is preferably sodium tungstate. However, other transition metal oxidation catalysts can be used, such as, for example, selenium dioxide, methyltrioxorhenium, and the like.

Steps (a) and (b) of the two-step synthesis are preferably conducted in the same reaction vessel, but can be conducted in separate reaction vessels, if desired. Step (b) is typically conducted in the same solvent as used in step (a), but additional solvent can be added in step (b), if desired.

The one-step process for producing the 2-hydrocarbyl-5-arylisoxazolidine simply involves including vinylaromatic compound as another ingredient used in forming the reaction mixture of the nitrone synthesis described above.

Vinyl aromatic compounds that can be used in either the one-step or two-step process include styrene, 2-methylstyrene, 3-methylstyrene, 4-methylstyrene, any of the various ar-dimethyl, ar-trimethyl, and ar-tetramethylstyrenes, pentamethylstyrene, α-methylstyrene, α,2-dimethylstyrene, α,3-dimethylstyrene, α,4-dimethylstyrene, any of the various ar-dimethyl, ar-trimethyl and ar-tetramethyl-α-methylstyrenes, pentamethyl-α-methylstyrene, and analogous compounds in which one or more higher alkyl groups are present in lieu of or in addition to the methyl groups of the foregoing compounds, vinylnaphthalene, 2-methoxystyrene, 3-methoxystyrene, 4-methoxystyrene, 3-ethoxystyrene, 2-trifluoromethylstyrene, 2,6-dichlorostyrene, 3-methylthiostyrene, 2-nitrostyrene, and in general, vinylaromatic compounds having up to about 18 carbon atoms in the molecule.

The one-step and the second step of the two-step reaction can be carried out in bulk (no added ancillary solvent) or it can be conducted in an ancillary solvent or diluent such as water, methanol, ethanol, butanol 2-methylpropanol, dioxane, tetrahydrofuran, or the like. Temperatures in the range of about 20 to about 140° C. and reaction periods in the range of about 0.5 to about 24 hours are typical. The reaction involves one mole of vinylaromatic compound per mole of hydrocarbylnitrone and thus if either reactant is present in less than a stoichiometric amount, it becomes the limiting reactant. Typically the amount of vinylaromatic compound used in forming the reaction mixture will fall in the range of about 1 to about 5 moles per mole of hydrocarbylnitrone being used or formed in situ. Hydrocarbylnitrone can be analyzed in the reaction mixture by $^1$H NMR (internal standard) using solvent suppression techniques. It is desirable to stir or otherwise agitate the reaction mixture during at least a substantial portion of the reaction period.

Recovery of the 2-hydrocarbyl-5-arylisoxazolidine from the reaction mixture can be effected in various ways. One convenient procedure comprises extracting the reaction mixture with a suitable relatively volatile organic solvent such as chloroform, methylene chloride, toluene, ethyl ether, or the like; drying the organic phase with a suitable solid state, neutral or basic, water absorbent such as potassium carbonate, sodium carbonate, sodium sulfate, or the like; removing the absorbent such as by filtration, centrifugation, decantation, or like procedure; and stripping off the solvent and any excess styrene under suitable temperature and pressure conditions.

Examples 6–10 presented hereinafter illustrate procedures for carrying out the two-step process (Example 6) and the one-step process (Examples 7–10).

Another embodiment of this invention comprises hydrogenating the 2-hydrocarbyl-5-arylisoxazolidine to form an N-hydrocarbyl-3-aryl-3-hydroxypropylamine. This reaction is preferably conducted using hydrogen and a palladium-carbon catalyst, and is readily conducted in a suitable solvent such as a liquid alkanol.

Further more specific embodiments of this invention include: (i) processes for the preparation of 2-methyl-5-phenylisoxazolidine that can be used in the preparation of N-methyl-3-phenyl-3-hydroxypropylamine, (ii) processes for the preparation of N-methyl-3-phenyl-3-hydroxypropylamine that can be used in the preparation of N-methyl-3-phenyl-3-[4-trifluoromethyl)phenoxy]propylamine and acid addition salts thereof, and (iii) processes for the preparation of N-methyl-3-phenyl-3-[4-trifluoromethyl)phenoxy]propylamine and acid addition salts thereof. These embodiments will now be considered seriatim.

Further Embodiment (i)

In this embodiment 2-methyl-5-phenylisoxazolidine is formed in either the one-step or two-step process described above using methylamine, formaldehyde, and styrene as the reactants. The reaction of N-methylnitrone with styrene results in the formation of 2-methyl-5-phenylisoxazolidine, and when properly performed, 2-methyl-5-phenylisoxazolidine can be produced in high yields.

Example 6 illustrates the practice of this embodiment as a two-step process. Examples 7–10 illustrate the one-step process.

EXAMPLE 6

A mixture of styrene (37.0 g, 356 mmol) and the N-methylnitrone solution from Example 5 is heated at 85° C. for 4 hours. After cooling, the phases were separated and the aqueous phase is extracted with chloroform (2×50 g). The combined chloroform extracts were combined with the initial organic phase, and the resultant mixture is washed with water (50 g). The organic phase is dried (K$_2$CO$_3$) and stripped of chloroform and excess styrene to give 2-methyl-5-phenylisoxazolidine (ca. 16 g).

EXAMPLE 7

Water (18.6 g), 33% $MeNH_2$ in EtOH (5.0 g, 53 mmol), $NaHC_3O$ (1.4 g, 17 mmol), formalin (4.3 g, 53 mmol), $NaWO_4.2H_2O$ (0.23 g, 0.7 mmol), and styrene (5.5 g, 53 mmol) were heated to reflux. Fifty per cent $H_2O_2$ (3.8 g, 56 mmol) is added dropwise to maintain reflux. After the addition, GC analysis indicated a 72:27 area % ratio of styrene:2-methyl-5-phenylisoxazolidine.

EXAMPLE 8

Paraformaldehyde (1.6 g, 53 mmol) was slowly added to 33% $MeNH_2$ in EtOH (5.0 g, 53 mmol) with cooling. Styrene (5.5 g, 53 mmol) and $NaWO_4.2H_2O$ (0.2 g, 0.6 mmol) were added and the solution is heated to reflux. Fifty per cent $H_2O_2$ (3.8 g, 55.9 mmol) was added dropwise to maintain reflux. After the addition, GC analysis indicated a 67:27 area % ratio of styrene: 2-methyl-5-phenylisoxazolidine.

EXAMPLE 9

Paraformaldehyde (21.7 g, 723 mmol) was added to 33% $MeNH_2$ in EtOH (68.0 g, 724 mmol) in one portion (exothermic). Styrene (75.1 g, 722 mmol) and $NaWO_4.2H_2O$ (3.4 g, 10 mmol) were added and the solution was heated to reflux. Fifty percent $H_2O_2$ (50.0 g, 735 mmol) was added dropwise over 4 hours to maintain reflux. After cooling, brine was added and the phases were separated. The lower aqueous layer was extracted with $CHCl_3$ and the $CHCl_3$ was removed to give a brown oil (5.5 g). The upper organic layer was stripped of styrene to give a brown oil (49.3 g). The two products (2-methyl-5-phenylisoxazolidine) were combined to give 54.8 g, 46% yield based on $MeNH_2$.

EXAMPLE 10

Paraformaldehyde (20.0 g, 724 mmol) was added in portions to 33% $MeNH_2$ in EtOH (68.0 g, 724 mmol). Styrene (75.0 g, 721 mmol) and $NaWO_4.2H_2O$ (3.4 g, 10 mmol) were added and the solution was heated to reflux. Fifty per cent $H_2O_2$ (50.0 g, 735 mmol) was added dropwise over 2 hours. After cooling, the phases were separated and the lower aqueous phase was extracted with ether (3×100 mL). The upper organic layer was combined with the ether extracts and washed with brine (2 x 100 mL). The ether and excess styrene were removed in vacuo to give (2-methyl-5-phenylisoxazolidine) as a brown oil (34.3 g, 29% based on $MeNH_2$).

Further Embodiment (ii)

In this embodiment 2-methyl-5-phenylisoxazolidine from Further Embodiment (i) is subjected to hydrogenation such that N-methyl-3-phenyl-3-hydroxypropylamine is formed. The hydrogenation can be effected by in situ generation of hydrogen, for example by use of finely divided zinc and aqueous acetic acid. Preferably, however, the hydrogenation is effected catalytically by use of hydrogen and a suitable catalyst such as palladium on carbon.

When generating the hydrogen in situ, a mixture consisting essentially of 2-methyl-5-phenylisoxazolidine, water, acetic acid and finely-divided zinc is maintained at one or more temperatures in the range of about 50 to about 100° C. for a sufficient period of time for N-methyl-3-phenyl-3-hydroxypropylamine to be formed in an appropriate yield (e.g., at least 80%). Usually periods in the range of about 1 to about 12 hours will suffice. The amount of acetic acid and finely-divided zinc should be sufficient to generate at least 15% excess hydrogen over the stoichiometric amount required for the reaction.

The catalytic hydrogenation preferably uses 5% or 10% palladium on carbon as catalyst and hydrogen pressures in the range of about 10 to about 100 psig at temperatures in the range of about 20 to about 80° C. However, other suitable hydrogenation catalysts may be used. The reaction should be conducted under essentially anhydrous conditions and thus at least substantially all of the water present in the reaction mixture from b) should be separated or removed, e.g., by a phase cut between the organic and aqueous phases, preferably followed by drying using a suitable solid state, neutral or basic, water absorbent such as potassium carbonate, sodium carbonate, sodium sulfate, or the like. Effective catalytic quantities of palladium-carbon catalyst are typically in the range of about 0.1 to about 5.0 wt % of the weight of the 2-methyl-5-phenylisoxazolidine be used in the reaction. Reaction periods in the range of 2 to about 24 hours are typical, with the lower temperatures and pressures usually requiring the longer reaction periods, and vice versa. Completion of the reaction is indicated by cessation of hydrogen uptake.

Examples 11–14 serve to illustrate ways by which 2-methyl-5-phenylisoxazolidine can be converted into N-methyl-3-phenyl-3-hydroxypropylamine by means of a suitable hydrogenation step.

EXAMPLE 11

2-Methyl-5-phenylisoxazolidine (2.0 g, 12.3 mmol) and Zn powder (1.2 g, 18.3 mmol) in 10 molar aqueous acetic acid are heated to 65–70° C. for 4 hours. Additional Zn powder (0.4 g, 6.1 mmol) is added and heating is continued for one more hour. The reaction mixture is neutralized with sodium hydroxide and extracted with chloroform. The extract is dried ($K_2CO_3$) and concentrated to give N-methyl-3-phenyl-3-hydroxypropyl-amine.

EXAMPLE 12

2-Methyl-5-phenylisoxazolidine (12.6 g, 77.3 mmol) in EtOH (134 g) is mixed with 5% Pd/C (1.2 g) in a glass pressure reactor. The reactor is warmed to 40–50° C. and the pressure is maintained at 40 psig with $H_2$ until the pressure becomes constant (ca. 24 hours). The mixture is filtered through Celite and the solvent is removed to give N-methyl-3-phenyl-3-hydroxypropylamine.

EXAMPLE 13

2-Methyl-5-phenylisoxazolidine (38.1 g, 234 mmol) dissolved in tetramethylene sulfone (38.1 g) is mixed with 5% Pd/C (1.9 g) in a glass pressure reactor. The reactor is warmed to 50° C. and the pressure is maintained at 40 psig with $H_2$ for 24 hours. Ethanol (38.1 g) is added and heating is continued for 48 hours. After cooling, the mixture is filtered and the EtOH is removed to give a solution of N-methyl-3-phenyl-3-hydroxypropylamine in tetramethylene sulfone.

EXAMPLE 14

2-Methyl-5-phenylisoxazolidine (54.3 g, 333 mmol) and Pd/C (2.7 g) in EtOH (55.0 g) are heated to 60–80° C. in a stirred (700 rpm) 300-mL Hastalloy autoclave which is kept pressurized to 55 psig with $H_2$ for 5 hours. After cooling, the mixture is filtered and the EtOH removed in vacuo to give N-methyl-3-phenyl-3-hydroxypropylamine.

Further Embodiment (iii)

This embodiment of the present invention comprises forming 2-methyl-5-phenylisoxazolidine as in Further Embodiment (i) above, forming N-methyl-3-phenyl-3-hydroxypropylamine as in Further Embodiment (ii) above, and then reacting N-methyl-3-phenyl-3-hydroxypropylamine so formed with a 4-halobenzotrifluoride to form N-methyl-3-phenyl-3-[(4-trifluoromethyl)phenoxy]propylamine. The 4-halobenzotrifluoride used in the last step of this sequence is preferably 4-fluorobenzotrifluoride or 4-chlorobenzotrifluoride. However, 4-bromobenzotrifluoride or 4-iodobenzotrifluoride, or combinations (or mixtures) of any two or of all four of these 4-halobenzotrifluorides can be used.

The reaction involves one mole of the 4-halobenzotrifluoride per mole of the N-methyl-3-phenyl-3-hydroxypropylamine. Therefore either reactant can be present in excess and the other becomes the limiting reactant. Typically the proportions of these reactants will be in the range of about 1 to about 2 moles of the 4-halobenzotrifluoride per mole of the N-methyl-3-phenyl-3-hydroxypropylamine. The reaction is best performed in a polar aprotic solvent such as sulfolane, N-methylpyrrolidinone, N,N-dimethylformamide, N,N-diethylformamide, N,N-dimethylacetamide, dimethylsulfoxide, or the like, to which a strong base in a finely-divided solid state, such as NaOH or KOH, has been added in an amount in the range of about 1.1 to about 1.5 moles per mole of N-methyl-3-phenyl-3-hydroxypropylamine used. If desired, a phase transfer catalyst such as tetrabutylammonium bromide, cetyltrimethylammonium chloride, tetrabutylammonium hydrogen sulfate, or the like can also be employed, typically in amounts in the range of about 0.1 to about 5.0 wt % based on N-methyl-3-phenyl-3-hydroxypropylamine.

Typically, the reaction is performed at one or more temperatures in the range of about 80 to about 150° C. Reaction periods are typically within the range of about 1 to about 24 hours. Upon completion of the reaction, it is desirable to add water to the mixture and to extract the solution with a suitable solvent such as ethyl ether or methylene chloride which is then washed with water until essentially all of the polar aprotic solvent is removed. Alternatively, the polar aprotic solvent can be removed by distillation, followed by a similar solvent extraction work up. The product is recovered by removal of the solvent, for example by distillation at reduced pressure. The N-methyl-3-phenyl-3-[4-trifluoro-methyl)phenoxy]propylamine can be converted to acid addition salts thereof by conventional procedures. For example, racemic fluoxetine can be formed by treating racemic N-methyl-3-phenyl-3-[4-trifluoromethyl)phenoxy]propylamine with anhydrous hydrogen chloride followed by low temperature crystallization (e.g., in the range of about 0 to about 30° C.) of the racemic fluoxetine from toluene solution.

Examples 15–17 serve to illustrate ways by which N-methyl-3-phenyl-3-[4-trifluoromethyl)phenoxy]propylamine can be formed by reaction between N-methyl-3-phenyl-3-hydroxypropylamine and 4-chlorobenzotrifluoride.

EXAMPLE 15

N-Methyl-3-phenyl-3-hydroxypropylamine (10.7 g, 64.8 mmol), 4-chlorobenzotrifluoride (13.0 g, 72.0 mmol), and NaOH (5.5 g, 138 mmol) are dissolved in N-methylpyrrolidinone (100 g), and the solution is heated to 130° C. for 24 hours. After cooling, water (200 mL) is added and the solution is extracted with ether (2×100 mL). The combined ether extracts are washed with water (6×50 mL), dried ($K_2CO_3$) and the solvent is removed in vacuo to give N-methyl-3-phenyl-3-[4-trifluoromethyl)phenoxy] propylamine as a brown oil. The oil is dissolved in toluene (150 mL) and anhydrous HCl is bubbled through the solution until saturated. Upon cooling to 0° C., crystallization occurs to give fluoxetine hydrochloride as a gray solid. The fluoxetine hydrochloride can be further purified by recrystallization from ethyl acetate/cyclohexane.

EXAMPLE 16

N-Methyl-3-phenyl-3-hydroxypropylamine (49.8 g, 302 mmol), 4-chlorobenzotrifluoride (60.0 g, 332 mmol), powdered 87% KOH (22.0 g, 341 mmol), and tetrabutylammonium hydrogen sulfate (0.5g, 1.5 mmol) and sulfolane (47 g) are combined and heated to 150° C. under a nitrogen condenser for 24 hours. More 4-chlorobenzotrifluoride (11.0 g, 61 mmol) and KOH (3.0 g, 47 mmol) are added and heating is continued for 48 hours. After cooling, water (300 mL) is added, and the aqueous solution is extracted with ether (3×100 mL) and the combined extracts are washed with water (2×100 mL). The ether solution is dried ($K_2CO_3$). The ether is removed in vacuo and the product is distilled (125–130° C., 0.5 mm Hg) to give N-methyl-3-phenyl-3-[4-trifluoromethyl)phenoxy]propylamine.

EXAMPLE 17

Powdered KOH (87%, 14.4 g, 257 mmol) is added to a mixture of N-methyl-3-phenyl-3-hydroxypropylamine (30.8 g, 187 mmol) and 4-chlorobenzotrifluoride (40.0 g, 221 mmol) in N-methylpyrrolidinone (100.0 g). The mixture is heated to 130° C. for 17 hours. The temperature is then raised to 150° C. and more KOH (6.5 g, 116 mmol) is added. Heating is continued for an additional 24 hours. More 4-chlorobenzotrifluoride (10.0 g, 55 mmol) is added and heating is continued for 10 hours. After cooling, water (200 mL) is added and the solution is extracted with $CH_2Cl_2$ (3×100 mL). The extract is washed with water (2×100 mL), dried $K_2CO_3$, and the solvent is removed in vacuo. The crude product is distilled (125–130° C., 0.5 mm Hg) to give N-methyl-3-phenyl-3-[4-trifluoromethyl)phenoxy] propylamine.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, formed in situ, blended or mixed with one or more other substances, components and/or ingredients in accordance with the present disclosure. Thus the fact that a substance, component or ingredient may have lost its original identity through a chemical reaction or transformation during the course of contacting, in situ formation, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises mixing together concurrently and/or in any sequence, and individually and/or in any subcombination(s), (i) one or more primary amines, (ii) one or more aldehydes or ketones, (iii) a transition metal-containing oxidation catalyst, and (iv) a peroxidic compound; and concurrently and/or subsequently, subjecting the mixture to, and/or maintaining the reaction mixture under, reaction conditions effective to form a reaction mixture in which a hydrocarbylnitrone has been formed.

2. A process according to claim 1 wherein (i) is a monoalkyl amine in which the alkyl group is a primary alkyl group.

3. A process according to claim 1 wherein (i) is methyl amine.

4. A process according to claim 1 wherein (ii) is a single aldehyde.

5. A process according to claim 1 wherein (ii) is formaldehyde or a formaldehyde precursor.

6. A process according to claim 1 wherein (ii) is formalin.

7. A process according to claim 1 wherein (iii) is sodium tungstate or one or more hydrates thereof.

8. A process according to claim 1 wherein (iv) is 10% or more aqueous hydrogen peroxide.

9. A process according to claim 1 wherein (iv) is 30% or more aqueous hydrogen peroxide.

10. A process according to claim 1 wherein (iv) is approximately 50% aqueous hydrogen peroxide.

11. A process according to claim 1 wherein (i) is a monoalkyl amine in which the alkyl group is a primary alkyl group, wherein (ii) is a single aldehyde, and wherein (iv) is 30% or more aqueous hydrogen peroxide.

12. A process according to claim 11 wherein (i) is methyl amine.

13. A process according to claim 1 wherein (i) is an alkyl amine in which the alkyl group is a primary alkyl group, wherein (ii) is formaldehyde or a formaldehyde precursor, and wherein (iv) is 30% or more aqueous hydrogen peroxide.

14. A process according to claim 13 wherein (i) is methyl amine.

15. A process according to claim 1 wherein (i) is an alkyl amine in which the alkyl group is a primary alkyl group, wherein (ii) is a single aldehyde, wherein (iii) is sodium tungstate or one or more hydrates thereof, and wherein (iv) is 30% or more aqueous hydrogen peroxide.

16. A process according to claim 15 wherein (i) is methyl amine.

17. A process according to claim 16 wherein (ii) is formalin.

18. A process according to claim 8 wherein the amount of hydrogen peroxide used in forming the mixture is about 1 equivalent relative to the amount of primary amine used in forming the mixture.

19. A process which comprises subjecting and/or maintaining a mixture formed from ingredients comprising (i) one or more primary amines, (ii) one or more aldehydes or ketones, (iii) one or more transition metal-containing oxidation catalysts, and (iv) one or more peroxidic compounds, to and/or under reaction conditions effective to form a reaction mixture in which a hydrocarbylnitrone has been formed.

20. A process according to claim 19 wherein (i) is a monoalkyl amine in which the alkyl group is a primary alkyl group, wherein (ii) is a single aldehyde, and wherein (iv) is 30% or more aqueous hydrogen peroxide.

21. A process according to claim 19 wherein (i) is methyl amine.

22. A process according to claim 19 wherein (i) is a primary alkyl amine in which the alkyl group is a primary alkyl group, wherein (ii) is formaldehyde or a formaldehyde precursor, and wherein (iv) is 30% or more aqueous hydrogen peroxide.

23. A process according to claim 22 wherein (i) is methyl amine.

24. A process according to claim 19 wherein (i) is a monoalkyl amine in which the alkyl group is a primary alkyl group, wherein (ii) is a single aldehyde, wherein (iii) is sodium tungstate or one or more hydrates thereof, and wherein (iv) is 30% or more aqueous hydrogen peroxide.

25. A process according to claim 24 wherein (i) is methyl amine.

26. A process according to claim 25 wherein (ii) is formalin.

27. A process according to claim 19 wherein the amount of peroxidic compound used in forming the mixture is about 1 equivalent relative to the amount of primary amine used in forming the mixture.

28. A process of according to claim 19 which further comprises concurrently and/or subsequently causing the hydrocarbylnitrone to react with one or more vinylaromatic compounds under reaction conditions effective to form a reaction mixture in which at least one 2-hydrocarbyl-5-arylisoxazolidine has been formed.

29. A process of according to claim 28 wherein said one or more vinylaromatic compounds is styrene.

30. A process of according to claim 23 which further comprises concurrently and/or subsequently causing the hydrocarbylnitrone to react with one or more vinylaromatic compounds under reaction conditions effective to form a reaction mixture in which at least one 2-hydrocarbyl-5-arylisoxazolidine has been formed.

31. A process of according to claim 30 wherein said one or more vinylaromatic compounds is styrene.

32. A process of according to claim 24 which further comprises concurrently and/or subsequently causing the hydrocarbylnitrone to react with one or more vinylaromatic compounds under reaction conditions effective to form a reaction mixture in which at least one 2-hydrocarbyl-5-arylisoxazolidine has been formed.

33. A process of according to claim 32 wherein (i) is methyl amine, wherein (ii) is formalin which, in forming said mixture, is used in an amount of about 1 equivalent relative to the amount of methyl amine used in forming the mixture, and wherein said one or more vinylaromatic compounds is styrene.

34. A process of according to claim 1 which further comprises mixing together (A) at least a portion of said reaction mixture and/or at least a portion of the hydrocarbylnitrone recovered from said reaction mixture, and (B) vinylaromatic compound, and subjecting and/or maintaining the mixture comprising ingredients (A) and (B) to reaction conditions effective to cause formation of 2-hydrocarbyl-5-arylisoxazolidine.

35. A process of according to claim 34 wherein (i) is methyl amine, wherein (ii) is formalin which, in forming said reaction mixture, is used in an amount of about 1 equivalent relative to the amount of methyl amine used in forming the mixture, and wherein said vinylaromatic compound is styrene.

36. A process of according to claim 35 wherein (iii) is sodium tungstate or one or more hydrates thereof, and wherein (iv) is 10% or more aqueous hydrogen peroxide.

37. A process which comprises mixing together as ingredients (i) one or more primary amines, (ii) one or more aldehydes or ketones, (iii) a transition metal-containing oxidation catalyst, (iv) a peroxidic compound, and optionally (v) a vinylaromatic compound; and concurrently and/or subsequently, subjecting the mixture to, and/or maintaining the mixture under, reaction conditions effective to form a reaction mixture in which:

a) if a vinylaromatic compound was included as an ingredient used in forming the mixture, a 2-hydrocarbyl-5-arylisoxazolidine has been formed, or b) if a vinylaromatic compound was not included as an ingredient used in forming the mixture, a hydrocarbylnitrone has been formed, and in which case the process further comprises mixing together as ingredients (A) at least a portion of said reaction mixture and/or at least a portion of said nitrone recovered from said reaction mixture, and (B) a vinylaromatic compound; and concurrently and/or subsequently, subjecting the mixture to reaction conditions effective to form a reaction mixture in which a 2-hydrocarbyl-5-arylisoxazolidine has been formed.

38. A process according to claim 37 wherein (i) is a monoalkyl amine in which the alkyl group is a primary alkyl group, wherein (ii) is a single aldehyde, and wherein (iv) is 30% or more aqueous hydrogen peroxide.

39. A process according to claim 37 wherein (i) is methyl amine.

40. A process according to claim 37 wherein (i) is a monoalkyl amine in which the alkyl group is a primary alkyl group, wherein (ii) is formaldehyde or a formaldehyde precursor, and wherein (iv) is 30% or more aqueous hydrogen peroxide.

41. A process according to claim 40 wherein (i) is methyl amine.

42. A process according to claim 37 wherein (i) is an alkyl amine in which the alkyl group is a primary alkyl group, wherein (ii) is a single aldehyde, wherein (iii) is sodium tungstate or one or more hydrates thereof, and wherein (iv) is 30% or more aqueous hydrogen peroxide.

43. A process according to claim 42 wherein (i) is methyl amine.

44. A process according to claim 43 wherein (ii) is formalin.

45. A process according to claim 37 wherein the amount of peroxidic compound used in forming the mixture is about 1 equivalent relative to the amount of primary amine used in forming the mixture.

46. A process according to claim 28 further comprising subjecting at least a portion of the reaction mixture in which at least one 2-hydrocarbyl-5-arylisoxazolidine has been formed and/or at least a portion of the 2-hydrocarbyl-5-arylisoxazolidine recovered therefrom to hydrogenation such that at least one N-hydrocarbyl-3-aryl-3-hydroxypropylamine is formed.

47. A process according to claim 28 further comprising:

A) subjecting (1) at least a portion of the reaction mixture in which at least one 2-hydrocarbyl-5-arylisoxazolidine has been formed and exists in whatever form it exists while in said reaction mixture, and/or (2) at least a portion of the 2-hydrocarbyl-5-arylisoxazolidine recovered from said reaction mixture, to hydrogenation such that there is formed (a) a reaction mixture in which at least one N-hydrocarbyl-3-aryl-3-hydroxypropylamine was formed and exists in whatever form it exists while in said last-named reaction mixture, and/or (b) at least one N-hydrocarbyl-3-aryl-3-hydroxypropylamine; and B) forming a mixture consisting essentially of at least a portion of (a) and/or (b) of A) hereof, and 4-halobenzotrifluoride, and subjecting the resultant mixture to, and/or maintaining the resultant mixture under, reaction conditions effective to produce a reaction mixture in which at least one N-hydrocarbyl-3-aryl-3-[4-trifluoromethyl)-phenoxy]propylamine is formed.

48. A process according to claim 37 further comprising subjecting at least a portion of the reaction mixture in which a 2-hydrocarbyl-5-arylisoxazolidine has been formed and/or at least a portion of the 2-hydrocarbyl-5-arylisoxazolidine recovered therefrom to hydrogenation such that at least one N-hydrocarbyl-3-aryl-3-hydroxypropylamine is formed.

49. A process according to claim 37 further comprising:

A) subjecting (i) at least a portion of the reaction mixture in which a 2-hydrocarbyl-5-arylisoxazolidine has been formed and exists in whatever form it exists while in said reaction mixture, and/or (ii) at least a portion of the 2-hydrocarbyl-5-arylisoxazolidine recovered from said reaction mixture, to hydrogenation such that there is formed (a) a reaction mixture in which at least one N-hydrocarbyl-3-aryl-3-hydroxypropylamine was formed and exists in whatever form it exists while in said last-named reaction mixture, and/or (b) at least one N-hydrocarbyl-3-aryl-3-hydroxypropylamine; and B) forming a mixture consisting essentially of at least a portion of (a) and/or (b) hereof, and 4-halobenzotrifluoride, and subjecting the resultant mixture to reaction conditions effective to produce a reaction mixture in which at least one N-hydrocarbyl-3-aryl-3-[4-trifluoromethyl)phenoxy]propylamine is formed.

50. A process according to claim 41 further comprising subjecting at least a portion of the reaction mixture in which at least one 2-hydrocarbyl-5-arylisoxazolidine has been formed and/or at least a portion of the 2-hydrocarbyl-5-arylisoxazolidine recovered therefrom to hydrogenation such that at least one N-methyl-3-aryl-3-hydroxypropylamine is formed.

51. A process according to claim 41 further comprising:

A) subjecting (i) at least a portion of the reaction mixture in which at least one 2-hydrocarbyl-5-arylisoxazolidine has been formed and exists in whatever form it exists while in said reaction mixture, and/or (ii) at least a portion of the 2-hydrocarbyl-5-arylisoxazolidine recovered from said reaction mixture, to hydrogenation such that there is formed (a) a reaction mixture in which at least one N-hydrocarbyl-3-aryl-3-hydroxypropylamine is formed and exists in whatever form it exists while in said last-named reaction mixture, and/or (b) at least one N-hydrocarbyl-3-aryl-3-hydroxypropylamine; and B) forming a mixture consisting essentially of at least a portion of (a) and/or (b) hereof, and 4-halobenzotrifluoride, and subjecting the resultant mixture to, and/or maintaining the reaction mixture under, reaction conditions effective to produce a reaction mixture in which at least one N-hydrocarbyl-3-aryl-3-[4-trifluoromethyl)-phenoxy]propylamine is formed.

52. A process which comprises:

a) reacting (i) one or more primary amines, (ii) one or more aldehydes or ketones, and (iii) a peroxidic compound, in the presence of an added transition metal-containing oxidation catalyst to form a hydrocarbylnitrone;

c) reacting hydrocarbylnitrone from a) and styrene to form at least one N-hydrocarbyl-5-phenylisoxazolidine;

d) hydrogenating N-hydrocarbyl-5-phenylisoxazolidine from c) to form N-hydrocarbyl-3-phenyl-3-hydroxypropylamine; and e) reacting N-hydrocarbyl-3-phenyl-3-hydroxypropylamine from d) and 4-halobenzotrifluoride to form N-hydrocarbyl-3-phenyl-3-[4-trifluoromethyl)phenoxy]propylamine.

53. A process according to claim 52 wherein said one or more primary amines is methylamine, wherein said one or more aldehydes or ketones is formaldehyde, formalin and/or paraformaldehyde, wherein said peroxidic compound is hydrogen peroxide, wherein said oxidation catalyst is sodium tungstate or one or more hydrates thereof, wherein the hydrogenation of d) is catalytic hydrogenation performed with hydrogen and a hydrogenation catalyst, and wherein said 4-halobenzotrifluoride is 4-chlorobenzotrifluoride or 4-bromobenzotrifluoride, or both.

54. A process which comprises mixing together as ingredients (i) methylamine, (ii) formaldehyde or a precursor of formaldehyde, (iii) a transition metal-containing oxidation catalyst, (iv) a peroxidic compound, and optionally (v) styrene; and concurrently and/or subsequently, subjecting the mixture to, and/or maintaining the mixture under, reaction conditions effective to form a reaction mixture in which:

a) if styrene was included as an ingredient used in forming the mixture, N-methyl-5-phenylisoxazolidine has been formed, or b) if styrene was not included as an ingredient used in forming the mixture, N-methylnitrone has been formed, and in which case the process further comprises mixing together as ingredients (A) at least a portion of said reaction mixture and/or at least a portion of N-methylnitrone recovered from said reaction mixture, and (B) styrene; and concurrently and/or subsequently, subjecting the mixture to reaction conditions effective to form a reaction mixture in which N-methyl-5-phenylisoxazolidine has been formed.

55. A process according to claim 54 wherein said peroxidic compound is hydrogen peroxide; wherein said oxidation catalyst is sodium tungstate or one or more hydrates thereof; wherein at least a portion of said reaction mixture in which N-methyl-5-phenylisoxazolidine has been formed and/or at least a portion of the N-methyl-5-phenylisoxazolidine recovered therefrom is subjected to catalytic hydrogenation performed with hydrogen and a hydrogenation catalyst to form N-methyl-3-phenyl-3-hydroxypropylamine; and wherein at least a portion of said N-methyl-3-phenyl-3-hydroxypropylamine is reacted with 4-halobenzotrifluoride to form N-methyl-3-phenyl-3-[4-trifluoromethyl)-phenoxy]propylamine.

* * * * *